United States Patent [19]

Roland

[11] Patent Number: 5,424,033
[45] Date of Patent: Jun. 13, 1995

[54] PROCESS AND AUTOCLAVE SYSTEM FOR SIZE REDUCING AND DISINFECTING CONTAMINATED HOSPITAL REFUSE

[75] Inventor: Rolf E. Roland, Illingen, Germany

[73] Assignee: TEB Holding S.A., Wasserbillig, Luxembourg

[21] Appl. No.: 59,238

[22] Filed: May 7, 1993

[51] Int. Cl.[6] .......................... A61L 2/06; B02C 18/06
[52] U.S. Cl. ........................... 422/26; 422/33; 422/295; 422/309; 588/258; 241/606; 241/29; 241/23; 241/18
[58] Field of Search .................. 422/26, 33, 295, 309; 588/258; 241/18, 23, 29, DIG. 14, DIG. 38, 606, 46.11, 46.17

[56] References Cited

U.S. PATENT DOCUMENTS

| | | | |
|---|---|---|---|
| 2,708,074 | 5/1955 | Hoskins | 241/17 |
| 2,731,208 | 1/1956 | Dodd | 422/26 |
| 3,064,322 | 11/1962 | Lodge | 422/295 |
| 3,087,210 | 4/1963 | Neiss | 422/295 |
| 3,415,613 | 12/1968 | Wallden | 422/295 |
| 4,057,391 | 11/1977 | Yamaguchi | 422/26 |
| 4,578,185 | 3/1986 | Wilson et al. | 241/606 |
| 5,217,688 | 6/1993 | von Lersner | 422/309 |

*Primary Examiner*—Robert J. Warden
*Assistant Examiner*—Theresa T. Snider
*Attorney, Agent, or Firm*—Klaus Thoma

[57] ABSTRACT

A method and apparatus for comminuting and sterilizing infectious waste wherein the size reduction processes take place within the same sealed container within which the sterilization through vacuumization and saturated steam pressurization takes place. Between the vacuum cycle and the high-pressure steam cycle there is interposed an intermittent steam pressurization step to atmospheric pressure. The comminution of infectious waste material is carried out by a series of cutting, crushing and shearing elements which are arranged in a compact, stack-like fashion in a vertical arrangement with the bearing elements, clutch, gear and motor located outside the autoclave container and detachable therefrom, which allows ready access to the shredder stack which can be removed and exchanged in fully assembled fashion.

36 Claims, 8 Drawing Sheets

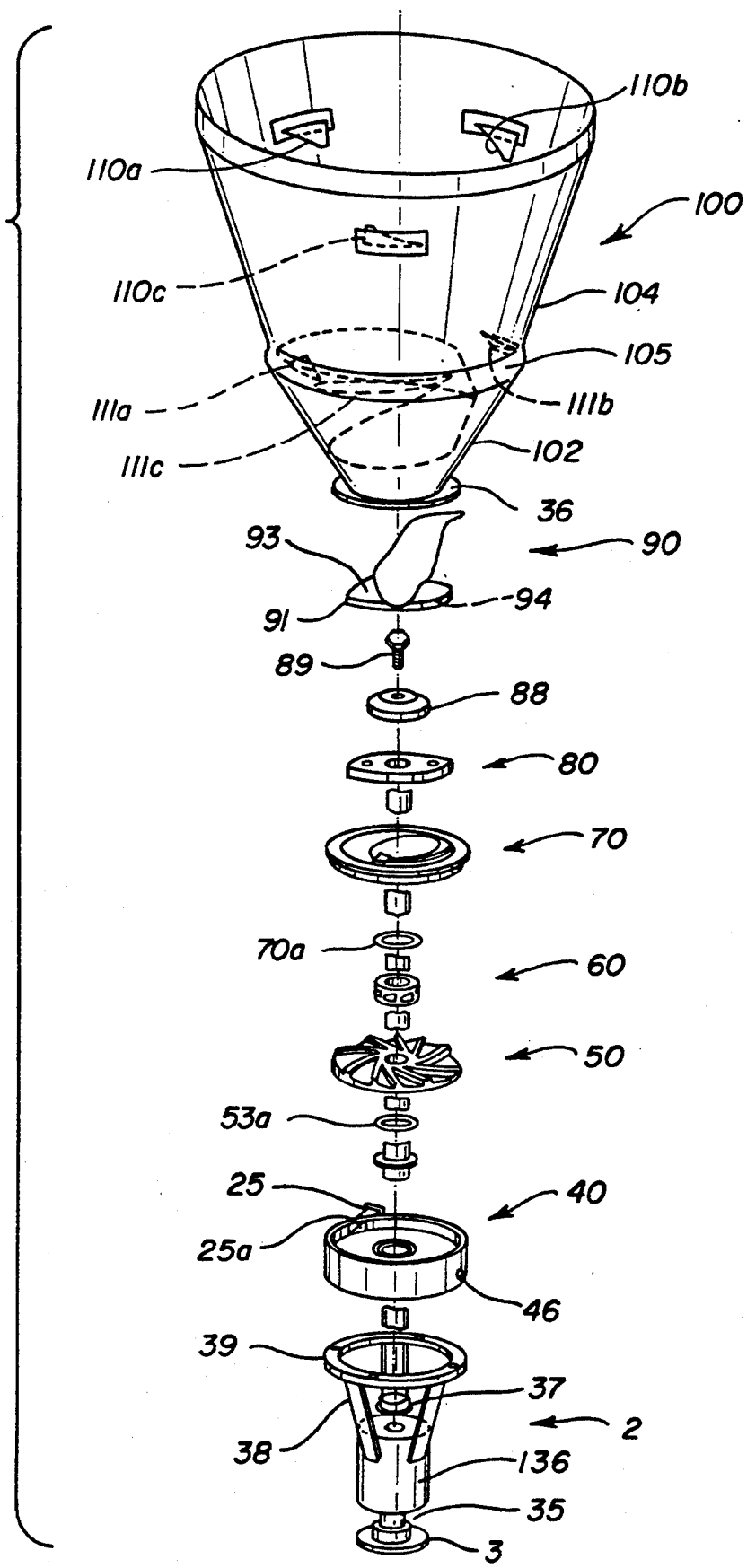

PROCESS AND AUTOCLAVE SYSTEM FOR SIZE REDUCING AND DISINFECTING CONTAMINATED HOSPITAL REFUSE

FIELD OF THE INVENTION

This invention concerns an apparatus and process for sterilizing and size-reducing contaminated hospital refuse, both in an autoclave system.

PRIOR ART

The treatment of infectious waste, especially hospital refuse, presents well-known problems, for which numerous solutions have been sought. Sterilization by exposure to steam is one of the preferred methods, as opposed to chemical treatment or incineration.

Steam is known to effectively kill all known pathogens, such as viruses, bacteria and bacilli, at least above certain temperatures (generally above 115 degree Celsius). Such pathogenic substances are embedded, however, in a variety of host media, or in trapped form, within the refuse typically generated by hospitals or doctors' offices. In addition, such refuse is often bagged in sealed containers or plastic bags, compounding the problems of effective steam treatment.

The two approaches known in the prior art are either autoclave systems, where steam is introduced into a hermetically sealed container wherein the refuse, as presented by the hospital, is exposed to one or more vacuum-steam pressure cycles for a sufficient length of time, or a combination of shredder/conveyor systems, wherein the refuse is first mechanically comminuted and then transported through a conveyor chamber within which continuous process steam is passed through and over the comminuted refuse for the duration of the dwell time in that chamber (flowing steam process).

All autoclave systems known in the prior art suffer from the inherent drawback, however, that the injected steam, even if introduced at great pressures, cannot very efficiently reach the non-comminuted waste material. On the other hand, if infectious waste were to be shredded first before being introduced in an autoclave system, the shredder itself, conveyors and other handling gear, etc., would present environmental risks of their own, which would have to be dealt with separately.

Conveyor systems for treating infectious waste also have some commonly known problems. For example, one system known in the prior art consists of two conveyor screws counter-rotating in two open halfshells, the walls of the halfshells being heated (German Utility Model 8702503). The use of screw conveyors has proved to be disadvantageous in operation, however, since the material to be disinfected is displaced laterally by the rotating movement of the spirals which tends to cause pile-ups and renders the contact surfaces of the heated walls of the halfshells ineffective.

An improvement upon the horizontal screw conveyor consist of so-called scrape conveyors with two endless link chains, which helps to eliminate the problem of the material to be handled piling up, which could lead to the heated contact surfaces to become exposed. Such conveyor chamber systems share the common characteristic of flowing steam process, however, which must, for the duration of the dwell cycle, be continuously injected and passed through the entire length of the conveyor chamber, which is much less effective than an autoclave system.

This is true even of the type shown in German "Gebrauchsmuster G 9112202.3", for example, a system which can be utilized in either a mobile or stationary form, wherein infectious hospital waste is first shredded and then treated with saturated steam. A small container is lifted, tilted and its contents emptied into a vertical entry tunnel. Upon closing of the entry tunnel lid, the waste is drawn through the action of a vertical shredder to the base of the shredder in a finally comminuted form. The comminuted waste is then transported by means of an elongated conveyor through a treatment tunnel wherein repeated steam and heat treatment over some prolonged period of time result in disinfection of the waste. For a non-autoclave system, this has proved to be a very effective treatment process.

SUMMARY OF THE INVENTION

The present invention provides a method and apparatus for introducing the disinfecting medium, i.e. saturated steam, into a hermetically sealed autoclave system, while at the same time comminuting the waste material within the selfcontained pressure vessel, thus opening up a much larger surface area to be efficiently disinfected during the vacuum-steam pressure cycle, while at the same time containing any contamination hazards within one hermetically sealed treatment area.

BRIEF DESCRIPTION OF THE INVENTION

It is an object of the present invention to provide an apparatus and method for treating infectious waste, including all body fluids such as blood, hemodialysis and renadialysis, surgical waste, sharps, laboratory waste (i.e. biological cultures, specimens, and vaccines), biological waste, contaminated waste from food products and other materials in a safe and totally self-contained manner.

In accordance with the preferred embodiment of the invention, containerized infectious waste is shredded and sterilized in an enclosed unit that is operated as an autoclave. As the waste-feed doors close, a vacuum is drawn on the electrically heated integrated shredder-/autoclave/sterilizer chamber ("SAS Unit"). Steam is then injected into the treatment chamber first from a steam storage chamber so as to bring pressure back up to atmospheric pressure, and then from the steam generator until an operating pressure of approximately 31 psig and a temperature of approximately 275 degrees Fahrenheit are reached. Simultaneously, a combination of uptake arms, stationary circumferential knives, rotary crushers and rotary disk vane shredders, all vertically positioned above one another within the intake chamber, begins pulling the waste downward while crushing and shredding it until the waste fragments are small enough to pass through a restricted waste ejection gate into a waste ejection chamber, which forms an integral part of the autoclave system and which is evacuated and pressurised the same as the intake/shredder chamber.

Sterilization of infectious waste is achieved by repeating the vacuum-steam injection/shredding cycle several times, e.g. three times, until all material is comminuted, sterilized and collected in the ejection chamber. For improved shredding action, the vertically aligned pull-down/crushing/shredding stack is operated intermittently in a stop-and-go fashion whereby its main direction of rotation is briefly reversed in order to free up any compacted or clogged up material.

It is especially advantageous in the preferred embodiment of the instant invention to locate the drive motor, reduction gear box and clutch outside and below the intake/shredder system, separated by sealing units which also shield the gear box and motor from the elevated temperatures of the shredder/autoclave unit. This arrangement allows very easy access to the components of high mechanical stress, such as uptake arm, cutting knives, crusher and shredder for quick maintenance, service and repair.

Since all of the walls of the autoclave intake/shredder unit and waste-ejection unit are heated, preferably by means of electric resistance coils, the vacuum phases are very effective in drying the waste material, which many times contain a high percentage of liquids, while the material is being treated as described. Because of this combination of drying and shredding action, the volume of infectious waste is reduced by approximately 80% during the disinfection process. In addition, moisture and thus weight is reduced substantially during the dehydration steps.

The air and steam removed from the autoclave chamber pass through an activated carbon filter and a High Efficiency Particle Arrestor (HEPA filter), which remove any particulate matter, odorous agents, and volatile organic compounds. The shredder-autoclave system of the present invention thus produces a dry, sterile, shredded, solid waste that is small enough to be non-recognizable as an infectious waste. This processed waste meets pre-treatment requirements for land disposals, waste-to-energy facilities or material recovery and recycling facilities.

The autoclave system of the present invention is preferably operated at approximately 31 psig pressure and approximately 275 degrees Fahrenheit, with a preferred residence time of app. 30 minutes, divided into three vacuum-shredding/steam pressure cycles. When operated in such manner, which may also be carried out continuously by means of a properly programmed process control computer, the system consistently achieves a 100% sterilization efficiencies for micro-organisms, including spores and highly virulent viruses. Typical micro-organisms deactivated include *Bacillus subtilis, Bacillus stearothermophilus, Enterococcus faecalis, Staphylococcus aureus, Clostridium botulinum, Pseudomonas aeruginosa, Coxsackie A virus, Echo virus,* Chrysosporium sp., *Cryptococcus albiudus,* Cryptosporidium sp., *Candida albicans,* Nocardia sp., *Mycobacterium fortunitum, Mycobacterium bovis,* Hepatitis B, Giardia sp., *Duck hepatitis virus.*

BRIEF DESCRIPTION OF THE DRAWINGS

Other objects and advantages of the invention will become apparent upon reading the following detailed description and upon reference to the drawings, in which:

FIG. 2 shows a three-dimensional exploded view of the shredder stack and treatment chamber of the present invention.

While the invention will be described in connection with the preferred embodiment and procedure, it will be understood that it is not intended to limit the invention to that embodiment or procedure. On the contrary, it is intended to cover all alternatives, modifications and equivalents as may be included within the spirit and scope of the invention as defined by the appended claims.

DESCRIPTION OF THE PREFERRED EMBODIMENT OF THE INVENTION

Figure 1:
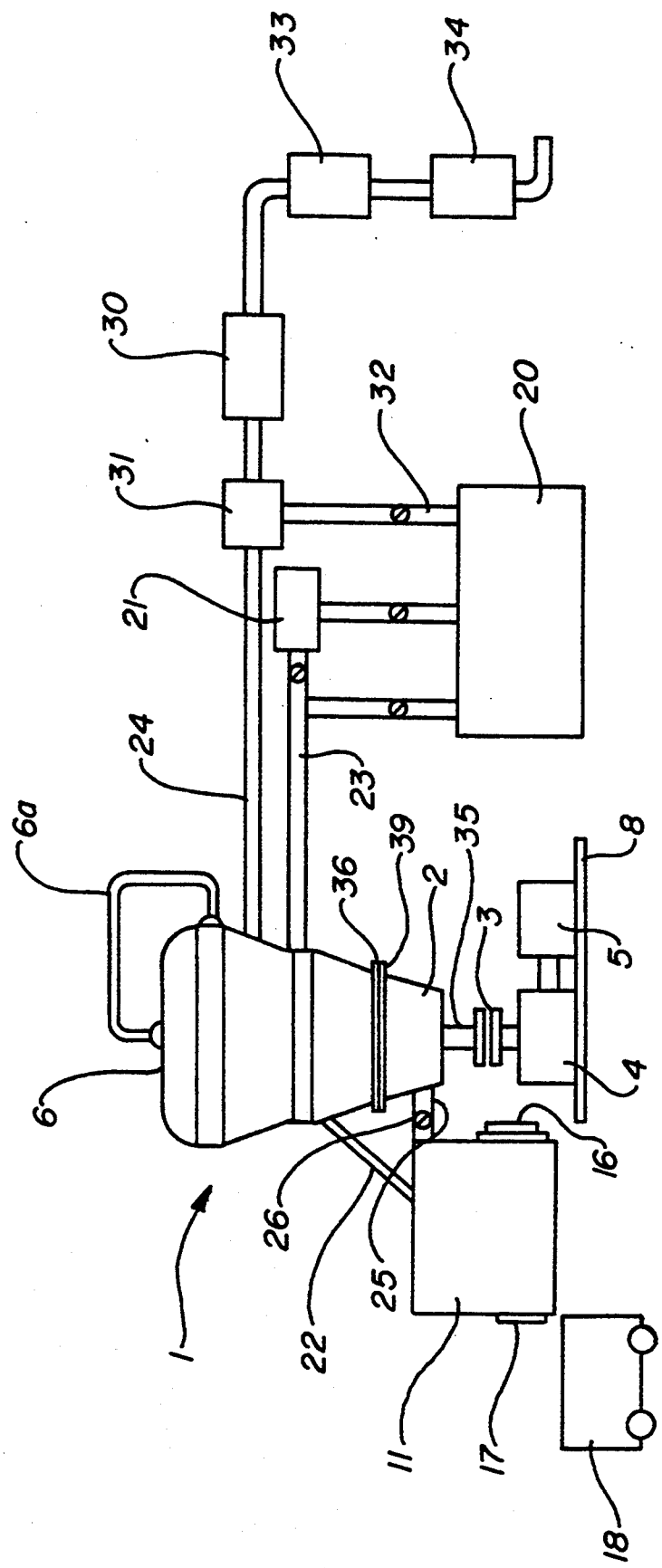
FIG. 1 shows a schematic depiction of the basic elements of the present invention.

The improved shredder/autoclave/sterilizer system of the present invention, as schematically depicted in FIG. 1, generally comprises an intake/shredder unit 1, which is connected via output channel 25 with waste ejection chamber 11. Intake/shredder unit 1 and chamber 11 are further connected through pressure equalization pipe 22 and are thus both communicably connected via pipe 23 to steam generating system 20 and via pipe 24 to vacuum pump 30.

Waste material is introduced into intake/shredder unit 1 by opening lid 6 by means of a hydraulic lifting mechanism 6a, which is also designed to hermetically seal off intake/shredder unit 1 prior to commencing operation.

The outer walls of intake/shredder unit 1 and waste ejection chamber 11 are heated externally, preferably by means of electric resistance coils (not shown) to a temperature of preferably 250° F., thus assuring that condensation of steam through wall contact is minimized while also elevating the temperatures of the waste material.

Once lid 6 is closed and sealed, pump 30 is activated to draw off almost all of the air from intake/shredder unit 1, as well as ejection chamber 11. The preferred pressure range for the vacuum phase is approximately 100 mbar.

This high vacuum assures that the viruses and bacilli are better exposed to the high-temperature steam cycle by removing as much as possible the protective layer of air around them. A virus, for example, is generally embedded in a host medium consisting of, e.g. fatty tissues or protein molecules. While the virus alone would normally be killed by raising the ambient temperature to 115 degree Celsius, the protein layer acts as a protective shield which hot air alone cannot easily crack, because air is known to be a poor heat conducting medium. Sterilization is therefore usually attempted by boiling in water or by exposing the contaminated medium to steam. Therefore, it is advantageous to eliminate the majority of the initial air volume present in the system, down to, e.g. 100 mbar, by activating vacuum pump 30 for approximately 3 minutes. Any airborne microorganisms present in this charge may be treated by externally heating pipe 24 and/or by injecting steam prior to filtration (not shown) or relying solely upon filter system 33 and 34, consisting of activated charcoal and HEPA filters, respectively.

Introducing steam into the partial vacuum thus created greatly enhances the effectiveness of the steam cycle/pressure cycle leading to more complete and quicker deactivation of pathogenic agents.

The duration of the vacuum phase is preferably three minutes, while the high-pressure steam cycle is preferably maintained for approximately five minutes. Before high-pressure steam is introduced into the partial vacuum of approximately 100 mbar, it has been found to be advantageous to add an intermittent steam filling phase, wherein the pressure is raised from the vacuum phase pressure of 100 mbar back to atmospheric pressure. A volume of steam sufficient to fill intake/shredder unit 1 and ejection chamber 11 back to atmospheric pressure is stored in a steam storage chamber 21, at preferably approximately 2 bar pressure and is first introduced into the intake/shredder unit 1 and ejection chamber 11. Subsequently, additional steam from the steam generation unit 20, wherein steam is stored at preferably 4.5 bar pressure, is introduced into intake/shredder unit 1 and waste injection chamber 11 so as to raise the pressure therein to a constant level of preferably approximately 2.2 bar. This intermittent steam refilling cycle prevents large quantities of condensation which could otherwise result from high-pressure steam directly from the steam generator being introduced into the autoclave system under vacuum. In the preferred embodiment of the invention, this intervening steam refilling cycle lasts approximately one minute.

An additional advantage of the vacuum cycling of the instant invention lies in the drying effect upon the contaminated material. Many times the waste to be treated contains liquids, such as, for example, blood, water or similar solutions which greatly add to the weight of the waste material. Through the combination of elevated wall temperatures, combined with the partial vacuum, liquids will more readily pass from the liquid phase to the gas phase and will thus easily be removed by the vacuum pump. Thus, while the waste material is being sterilized, it is also being dried, resulting in a much more light-weight, dry residue than would otherwise result from the continuous process-steam sterilization methods used in non-autoclave systems, wherein the material even absorbs additional moisture from the steam applied to it.

To assure complete deactivation of all pathogenic material, the vacuum-refilling-high pressure steam cycles are preferably repeated two more times.

The gases drawn by vacuum pump 30 are passed through a condenser unit 31 prior to passing through activated charcoal filter unit 33, so as to eliminate as much as possible all condensation liquids. The water collected in condenser unit 31 is reintroduced via pipe 32 at its still existing elevated temperature into the steam-generating unit 20, thus resulting in substantial energy savings.

The activated charcoal filter 33 traps and eliminates gases such as volatile organic carbohydrates. From there the gases pass through a system of HEPA filters which eliminate all remaining toxic agents and noxious fumes, as is well known in the art.

During the steam pressure cycle, motor 5 is activated to rotate, via gearbox 4 and clutch 3, the shredder shaft 35, which extends into intake/shredder unit 1 and upon which are located the shredder components described in more detail below.

The direction of motion of motor 5 is reversible and is preferably reversed for approximately 10 seconds every 60 seconds, thus automatically freeing up any materials which might have become clogged or stuck in the shredding unit.

The lower section 2 of autoclave chamber 1 contains, around shaft 35, a series of packing and sealing elements which seal off 1 against both the vacuum and high pressures which occur therein. Lower section 2 also provides a temperature shield between heated intake/shredder unit 1 and the temperature-sensitive gearbox 4 and motor 5. Lower section 2 is sealingly but removably attached to intake/shredder unit 1 at flange 36. After disengaging clutch 3, and pulling aside the motor and gearbox unit mounted on skid 8, lower section 2, together with the entire shredder stack (elements 40, 50, 60, 70, 80 and 90) may be removed and exchanged. This permits very easy and quick access to autoclave cheer 1 from below and also permits removal and exchange of all of the shredder components located on shaft 35. Cleaning and servicing of the shredder unit is thus made vastly more accessible and less costly a task than in any other shredder-sterilization system known in the prior art. In addition, the proper assembly and adjustment of the various components making up the shredder stack, which is crucial to proper operations, can all be done outside the unit and thus with much more ease and accuracy, prior to reassembly.

During each shredding and steam pressure cycle, a portion of the waste material within intake/shredder unit 1 is comminuted to a size which is predeterminable by the setting of restrictor gate 26 located within output channel 25 leading into ejection chamber 11. The setting of restrictor gate 26 assures sufficient back pressure upon the material being shredded and allows only waste matter which has been completely comminuted to that predetermined size to be pushed by the action of spiral vane cutter 50, described in more detail below, out of output channel 25 and into ejection chamber 11.

Once the last shredding/steam sterilization cycle is completed, the system pressure is lowered to atmospheric pressure and lid 6 and/or ejection gate 17 may be opened up. The comminuted, sterilized and dried material collected in chamber 11 is then removed, for example by activating hydraulic ejector means 16 for pushing the sterilized material through exit gate 17 out of chamber 11 and into, e.g., a collector bin 18.

Referring now to FIG. 2, a better understanding can be gained of the arrangement of the individual elements of the shredder stack inside intake/shredder unit 1. FIG. 2 also shows a more detailed arrangement of lower section 2, which is shown to consist of a bearing box 136 and sealing units 37, both mounted within frame 38 which is attached to flange 39.

Starting now from the top, the treatment chamber housing 100 is shown to comprise an upper conical section 104 and a lower conical section 102. On the inside of upper conical section 104 there are removably attached to the inner peripheral wall a series of, preferably three, stationary knives 110a, 110b and 110c respectively. These knives are generally triangularly shaped with sharpened cutting edges whose upper side is flat and the lower side downwardly sloped, such that objects which are cut are pushed downward. Stationary knives 110a, 110b and 110c are radially spaced approximately 120 degrees apart from one another but are not arranged vertically in the same plane, but rather at differing vertical positions within upper conical section 104. This assures that an elongated piece of material, which is spun around inside treatment chamber 100 is not cut three times in the same place but is instead cut into several pieces. As is also apparent from FIG. 2, one of the stationary knives, e.g. 100c, is pointing in the opposite rotational direction from the other two knives. This assures that when the rotational direction is reversed, material is still being cut while being dragged in the opposite direction.

The second set of such stationary knives, 111a, 111b and 111c, respectively, are arranged along the interior walls of the transitional cylindrical section 105 between upper conical section 104 and lower conical section 102 and/or within the inner peripheral walls of inner conical section 102. The same vertical and radial arrangement and directional positioning of cutting edges, which was described above for knives 110a, 110b and 110c holds true for the lower set of knives, even though the angular position of this second set of stationary wall knives is preferably in a different plane than the upper set of knives.

While the lower set of knives 111a, 111b and 111c are more directly interacting with the intake arm 90, it has being found to be advantageous to have an upper set of stationary peripheral knives since the rotation of intake arm 90 generally sets into motion the majority of the waste matter within treatment chamber 100 even if positioned well above intake arm 90.

Intake arm 90, which will be described in some more detail below, is mounted onto an intake arm base plate 91 which generally mirrors in shape the rotary crusher 80 and is mounted thereon with retaining bolts extending through the circular openings 93, 94, of intake arm base plate 91 respectively 83, 84, of rotary crusher 80, (shown in FIG. 7) as well as by means of head screw 89 and retainer ring 88.

Rotary crusher 80 in turn is biased against and rotates on top of central stationary cutter disk 70, which through its spiraling guiding surfaces and planar cutting edges further shreds and crushes the material as it is being pushed through the eccentric opening defined between its interior radial surfaces and shaft 35 downwardly into the space below central stationary cutter disk 70.

Biased against spacer disk 70a, cylindrical cutter ring 60 is mounted within the interior radial opening of central stationary cutter disk 70 and on top of spiral vane cutter 50. Spiral vane cutter 50, in turn, through intervening spacer disk 53a, is biased against and rotates within, spiral vane cutter housing 40. As is shown in FIG. 2, spiral vane cutter housing 40 has within its outer perimeter wall an outlet opening 25a which is attached to output channel 25, through which comminuted waste is moved into waste ejection chamber 11.

Figure 3A:
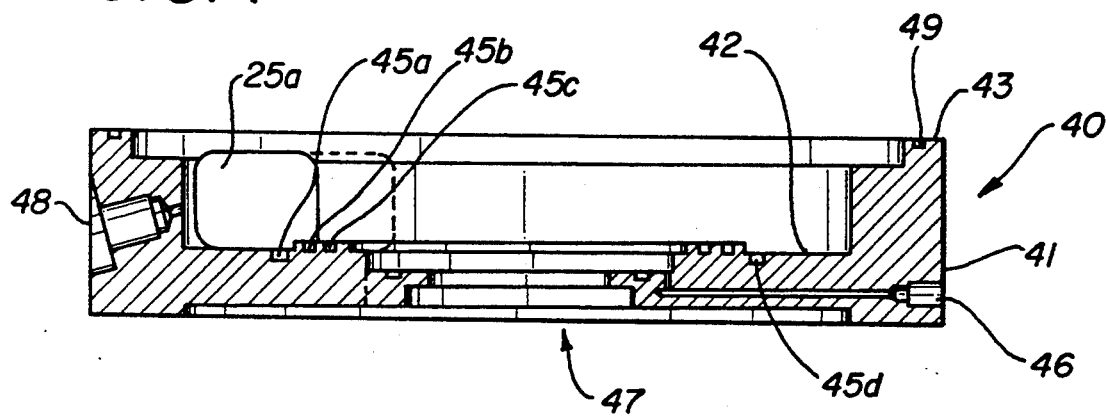
FIG. 3A is a cross sectional view of the spiral vane cutter housing, taken along line A—A of FIG. 3.
Figure 3:
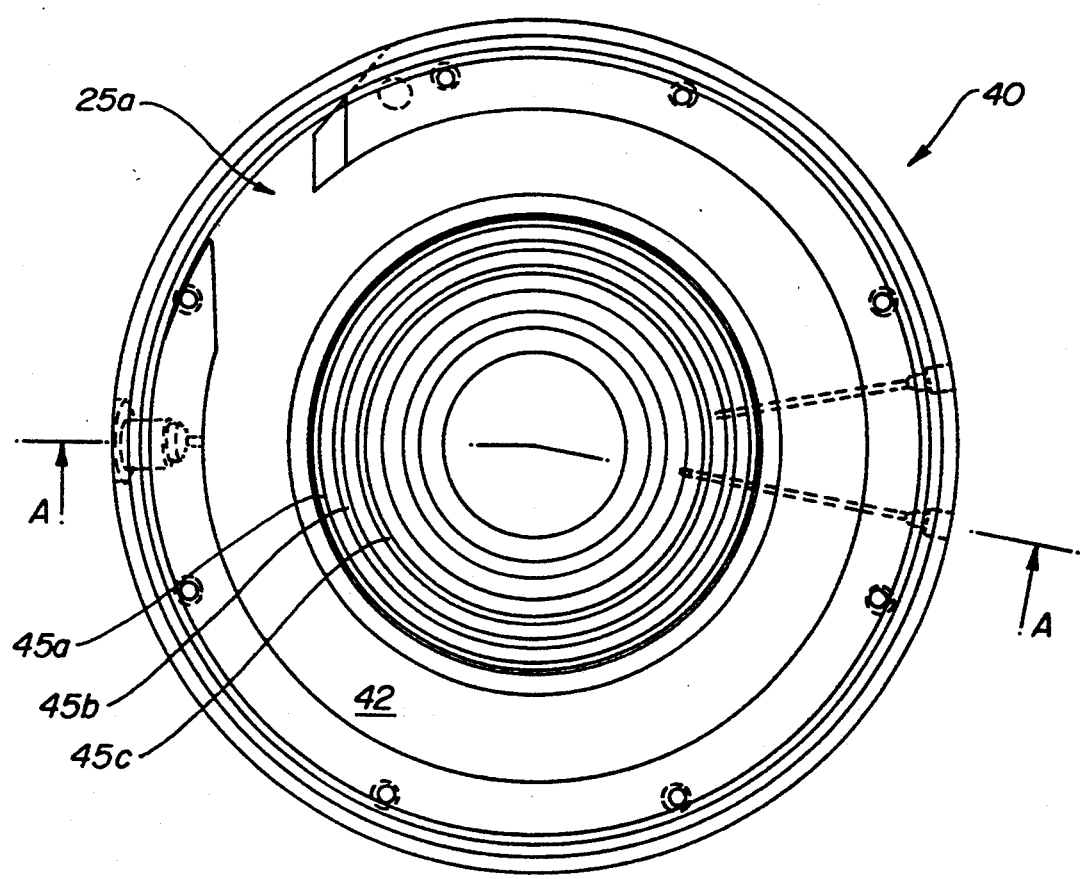
FIG. 3 is a plan view of the spiral vane cutter housing.
Figure 4:
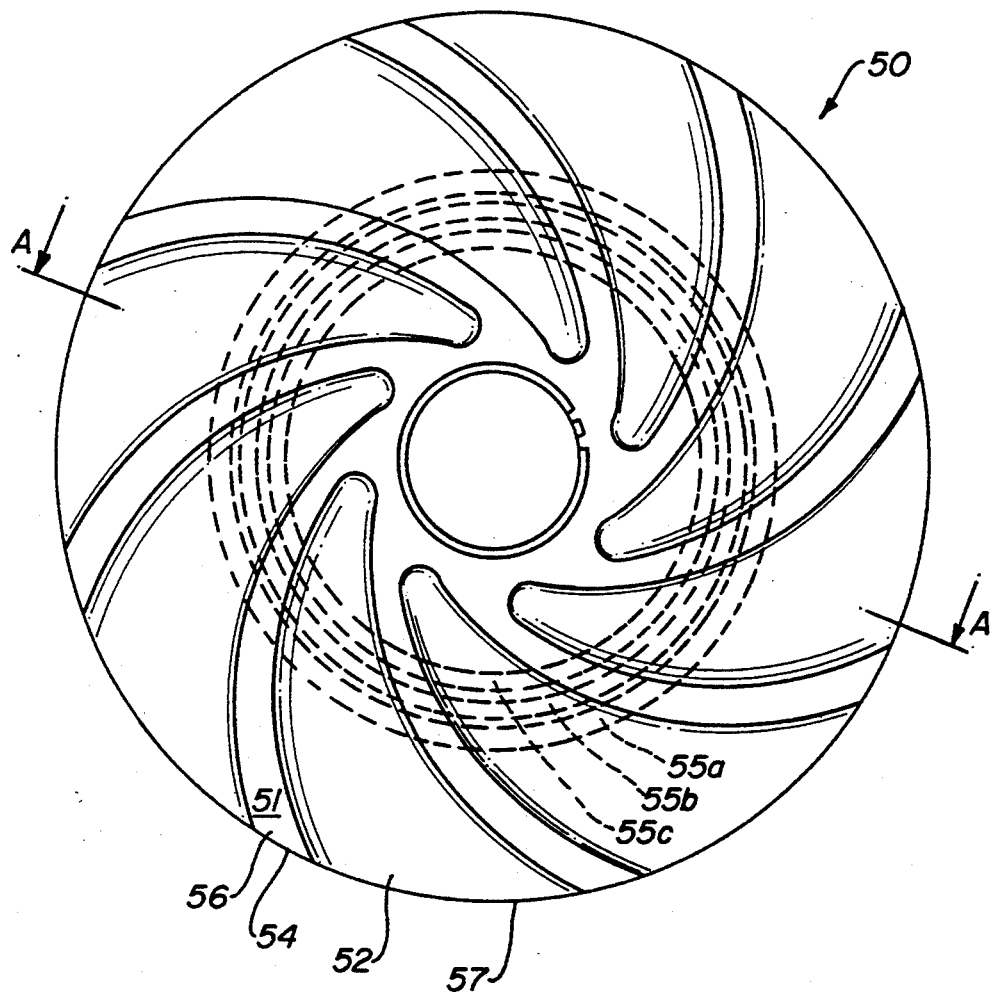
FIG. 4 is a plan view of the spiral vane cutter.
Figure 4A:
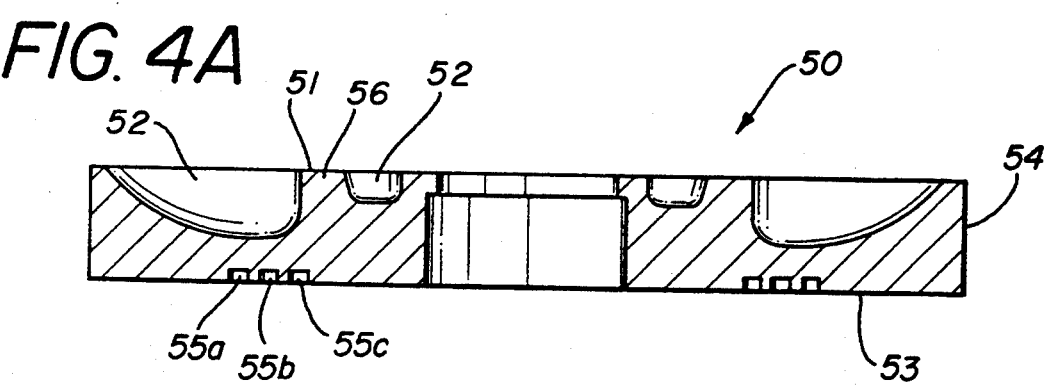
FIG. 4A is a cross sectional view of the spiral vane cutter, taken along line A—A of FIG. 4.

Referring now to FIG. 3, spiral vane cutter housing 40 possesses an interior lower annular surface 42 which is defined by cylindrical wall 43 and central cylindrical shaft opening 47. Protruding from interior lower annular surface 42 are annular ridges 45a, 45b, 45c respectively, which define a labyrinth sealing system which sealingly matches corresponding annular groves 55a, 55b and 55c, which are shown within the bottom surface 53 of spiral vane cutter 50, as shown in FIG. 4 and 4a. An additional sealing element is provided by annular channel 45d which is provided within lower interior annular surface 42 for receiving a packing cord (not shown).

Referring again to FIG. 3, there is also shown circumferential opening 25a within cylindrical wall 43, through which the comminuted waste particles are expelled by the motion of spiral vane cutter 50 and to which is attached exterior waste output channel 25 (not shown in FIG. 3).

The same elements just described are also shown in FIG. 3a, which represents a cross section through spiral vane cutter housing 40 along line A—A of FIG. 3. FIG. 3a also shows one of the seal ports 46 through which sealing material is introduced into the labyrinth seal areas of vane cutter housing 40.

There is also apparent in FIG. 3a a cross sectional view of remedial steam injector port 48. Steam ejector port 48 is used in cases where a problem occurs with the shredder while the system is in action, requiring interruption of the disinfection process and service of the shredder unit. Since in that case there might still be some material left within cutter housing 40 which is not able to pass through exit port 25a, additional high-pressure steam is injected through port 48 to be certain to disinfect all material before lower unit 2 is removed by loosening flange 36, making accessible the entire shredding unit which can then be removed for service. Removal for service requires the step of removing the duplex roller chain from clutch 3, moving the lower half of clutch 3, together with gearbox 4 and motor 5 to the side, loosening a series of bolts (in the preferred embodiment preferably eight) on flange 36, which then permits the entire assembly of the above referred to elements 40, 50, 60, 70, 80 and 90 to be pulled out of lower treatment chamber 102. Even though the radial extension of intake arm 90 is larger than the diameter of the opening of flange 36, the shredder unit may be tilted and thus be removed as one complete unit, including uptake arm 90, through the central opening of flange 36. Since the proper alignment and adjustment of the various components making up the shredder stack is critical to proper performance, it is made possible by the instant invention to dispense with servicing this shredder unit in the field. Instead, the entire shredder stack may be sent to the shop for service and/or repair, while the customer's unit is provided with an exchange shredder stack, thus minimizing downtime, expense and margin for error.

Also shown in FIG. 3a is an annular groove 49 within which a seal ring (not shown) is housed for sealingly engaging annular bottom surface 77 of central stationary cutter disk 70.

Referring now to FIG. 4 and 4a, spiral vane cutter 50 is shown as having a number of radially outwardly extending spiral vanes 51, which are defined by their upper planar cutting surfaces 56, circumferential end section 54 and radially outwardly down-spiraling cutouts 52, which are sloped down to lower circumferential base line 57. Also shown in FIG. 4 and FIG. 4a are annular grooves 55, 55b and 55c which form the matching sealing recesses for the annular labyrinth seal ridges 54a, 54b and 54c of spiral vane cutter housing 40.

Figure 5:
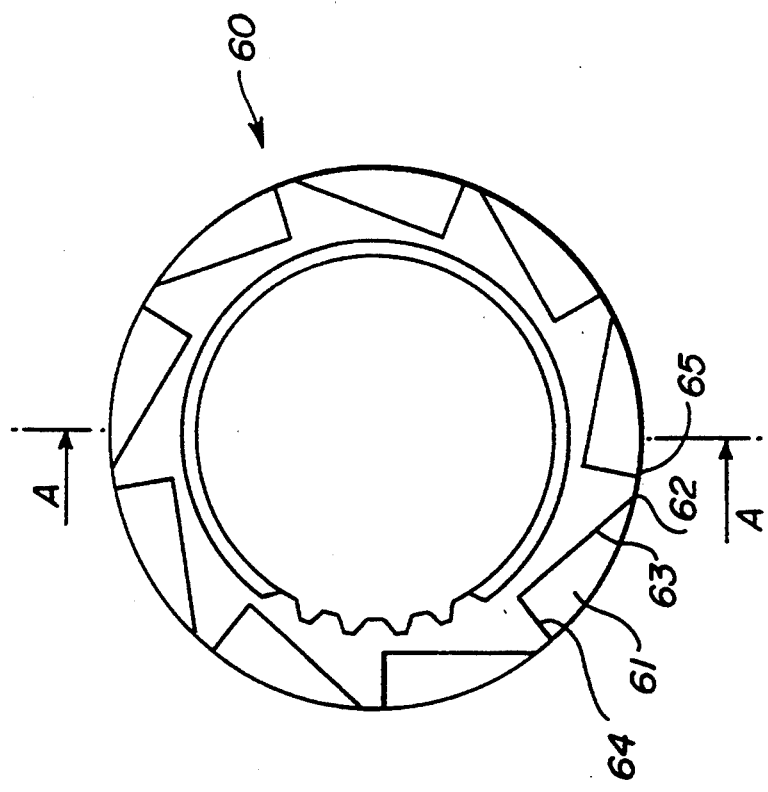
FIG. 5 is a plan view of the cylindrical cutter ring.
Figure 5A:
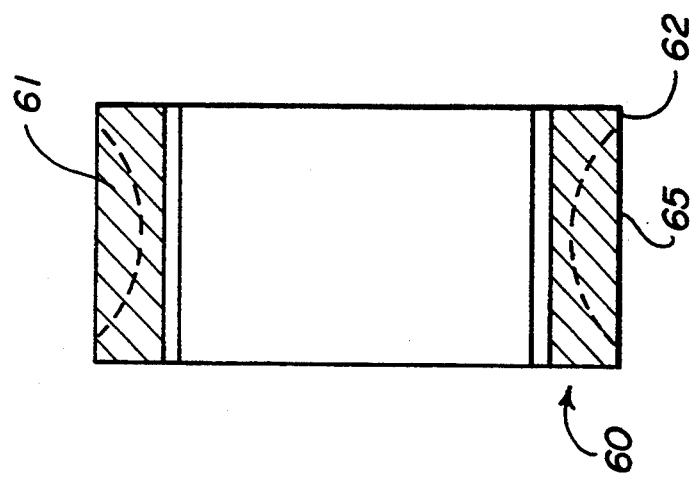
FIG. 5A is a cross sectional view of the cylindrical cutter ring, taken along line A—A of FIG. 5.

Referring now to FIG. 5 and 5a, cylindrical cutter ring 60 is shown as having within its outer peripheral surface 62 a plurality of machined recesses 61, which are defined by planar surface 63, rear wall 64 and cutting edge 65. As is apparent from the arrangement shown in these drawings, any material which might be slung around the periphery of cylindrical cutter ring 60 is cut when the direction of motion is reversed from, e.g., clockwise to counter-clockwise rotation.

Figure 6A:
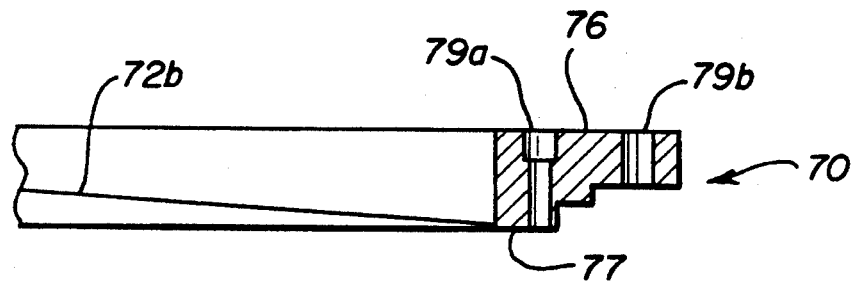
FIG. 6A is a cross sectional view of the stationary cutter disk, taken along line A—A of FIG. 6.
Figure 6:
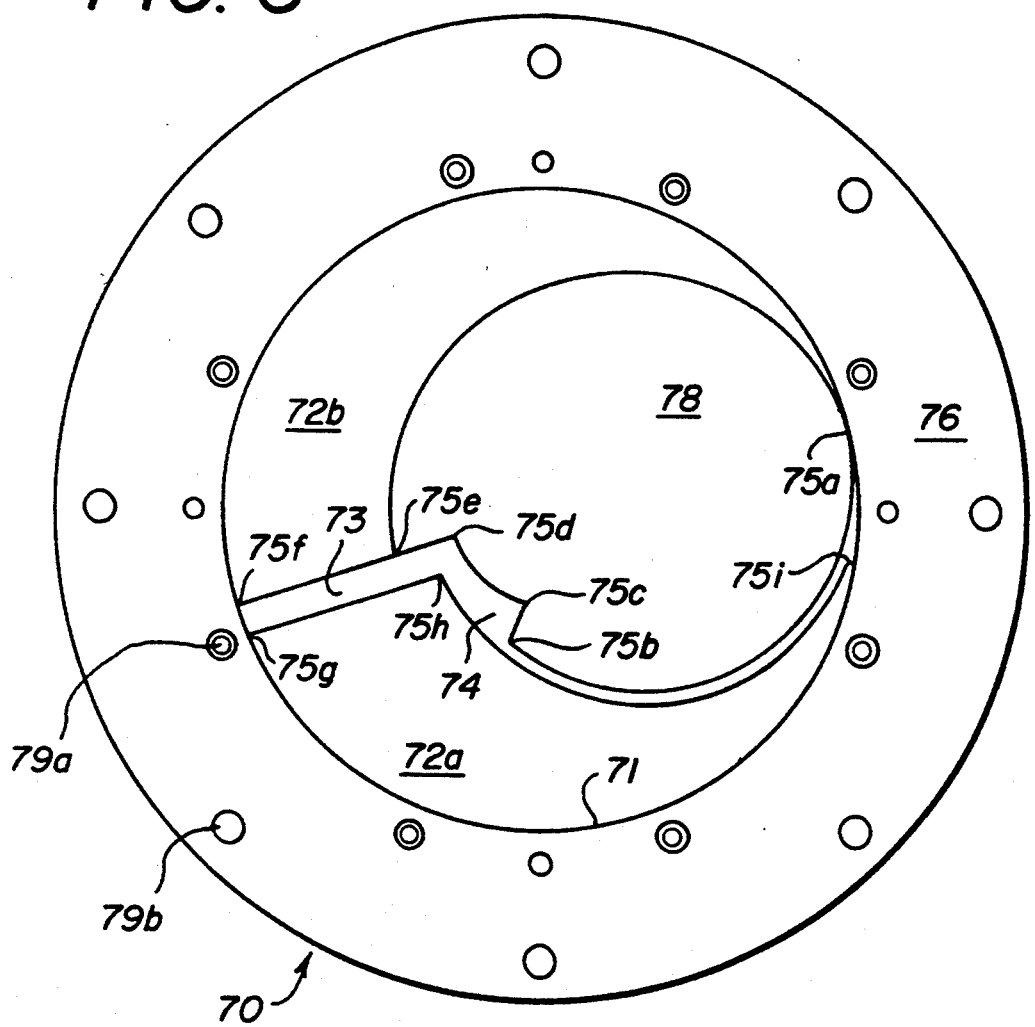
FIG. 6 is a plan view of the stationary cutter disk.

In FIG. 6 is provided a plan view and in FIG. 6a a cross sectional view through stationary cutter disk 70. Stationary cutter disk 70 has an upper annular surface 76 which, when the shredder stack is assembled, is biased against flange 36 of treatment chamber 100 and secured thereon by means of bolts extending through bore holes 79b. Upper surface 76 is also provided with bore holes 79a, which extend through to lower annular surface 77 which, when assembled, is biased against upper annular surface 43 of spiral vane cutter housing 40. There is also provided within upper surface 76 a circular cut-out 71, concentric with the outer perimeter of stationary cutter disk 70, which defines two radially sloping surfaces 72a and 72b, which are separated from one another by cutting surface 73. Cutting surface 73 is defined by points 75a, 75b, 75c, 75d, 75f, 75g, 75h and 75i. The planar surface contained within these points, of the shape as shown in FIG. 6, represents a horizontal cutting surface against which the material being introduced from above into space 78 and then carried forward along inclined surfaces 72a and 72b is cut and sheared. The radially interior section 74 of cutting ridge 73 is shaped in the form of an axially extended, downwardly pointed cutting edge. Surface 72a begins at point 75i and spirals down to point 75h, where it is a small step below upper surface 73 and also slopes radially outwardly in a spiral fashion to reach its lowest point at 75g. Sloping surface 72b, on the other hand, which at point 75f lies approximately 25 millimeters below the top of cutting ridge 73, is sloped upwardly from there on until it reaches at point 75a upper surface 76 again. Material which is drawn through the sweeping action of rotary crusher 80 into eccentric annular opening 78, is thus cut, sheared and crushed before being pushed through opening 78 into the space below and hence into spiral vane cutter 50.

Figure 7:
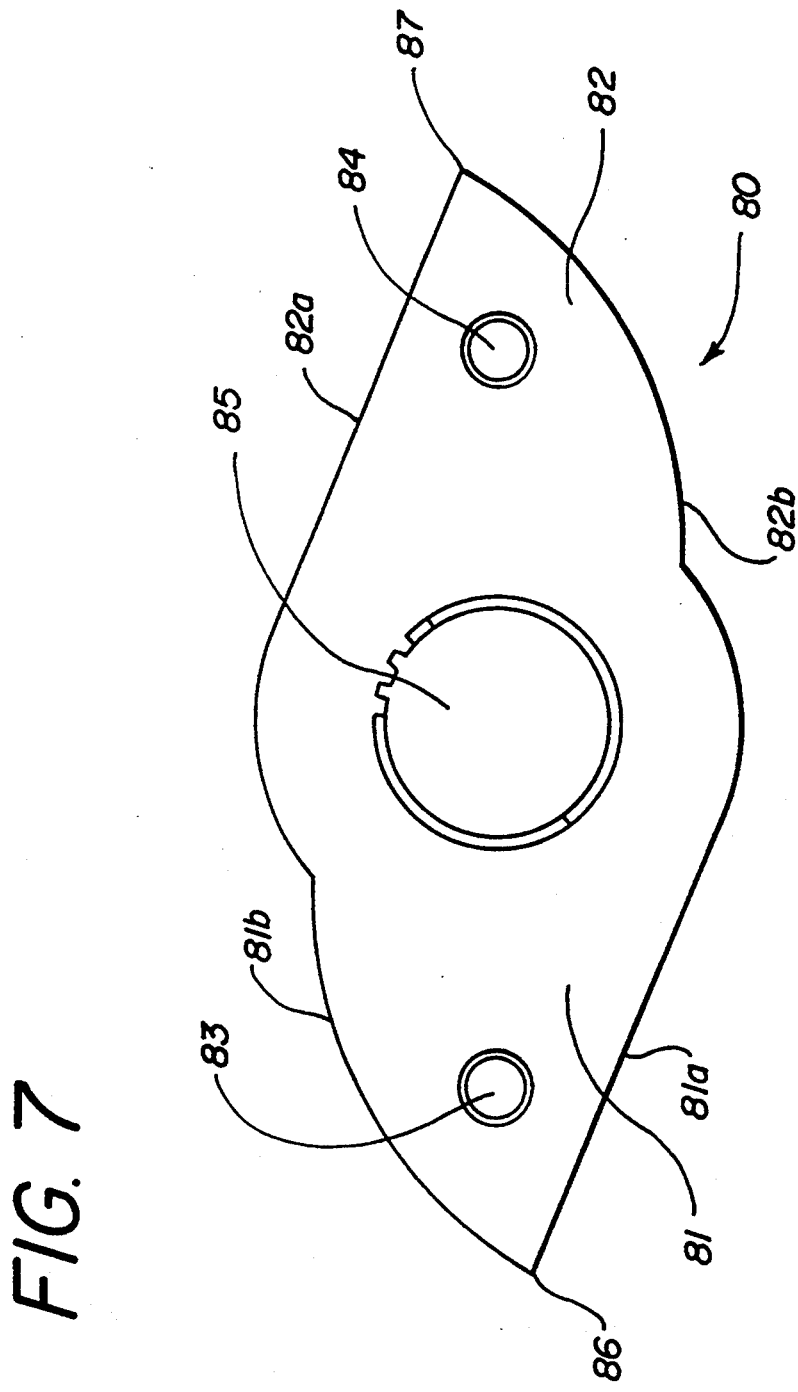
FIG. 7 is a plan view of the rotary crusher.

Referring now to FIG. 7, rotary crusher 80 is shown to a be solid metal plate cut into generally wing-shaped form with two mirror-image wings 81 and 82, as well as a central circular cut-out 85 for receiving shaft 35, as well as circular openings 83 and 84 for receiving retainer bolts with which intake arm base plate 91 is attached to rotary crusher 80. Edges 81a, 81b and 82a, 82b are sharpened to provide cutting edges and meet in sharply pointed tips 86 and 87.

Figure 8A:
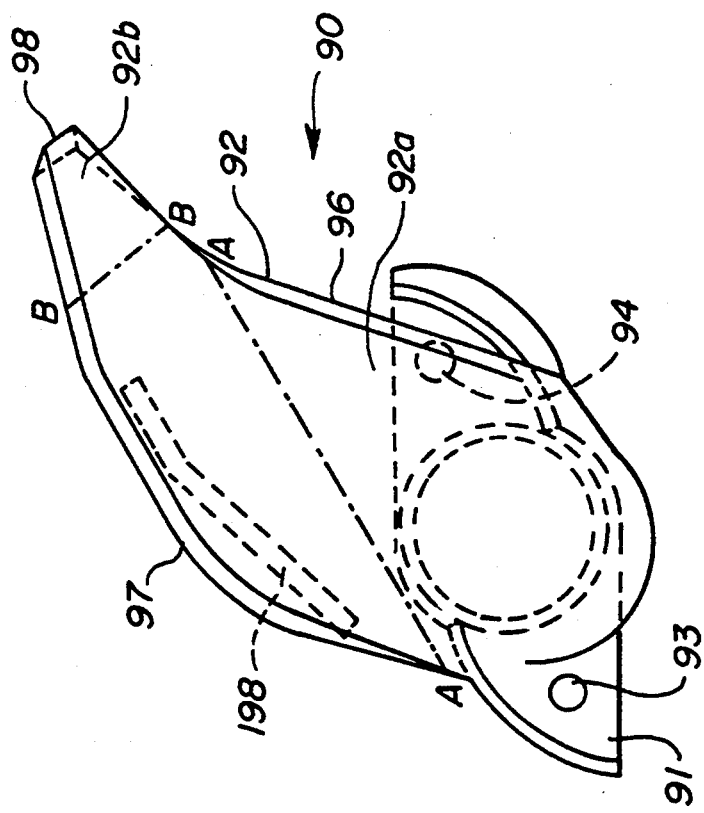
FIG. 8A is a plan view of the intake rake.
Figure 8B:
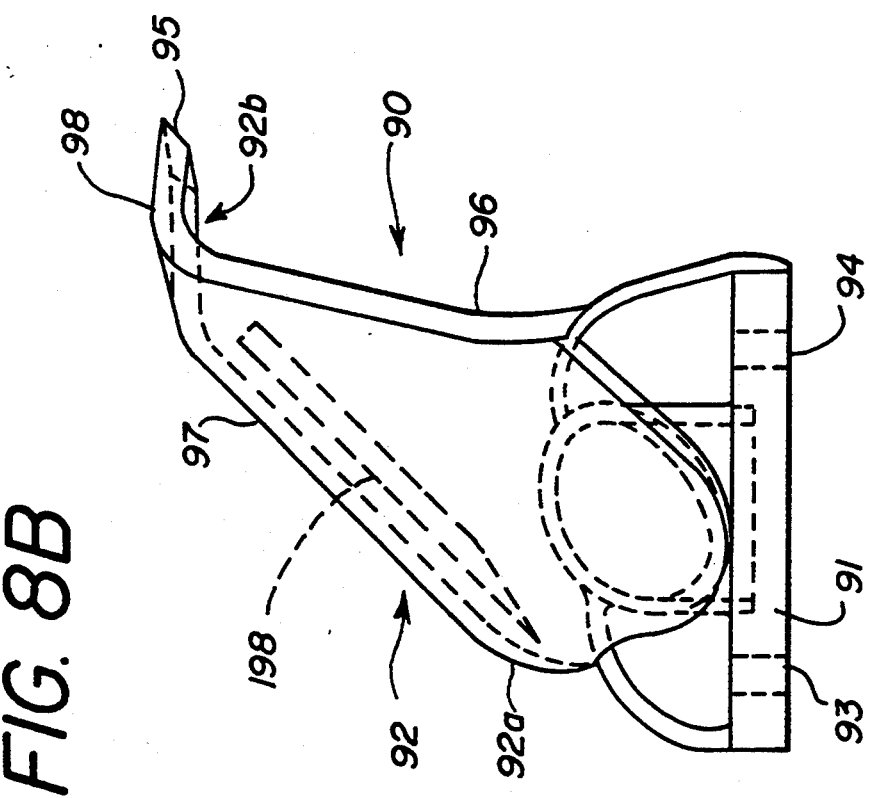
FIG. 8B is a side elevational view of the intake rake.

Referring now to FIG. 8a and FIG. 8b, intake arm 90 is mounted upon face plate 91 which is cut in the same shape as rotary crusher 80. Intake arm 90 generally consist of a radially upwardly inclined and upwardly tapered lower section 92a and a generally wing-like top section 92b, terminating in cutting edges 96 and 97, respectively in 95 and 98. This design has proven to be very advantageous in preventing waste material such as cloth or plastic hoses from wrapping around and getting entangled in the intake arm. When reversing the direction of rotation of shaft 35, such material would be forced upward towards the smaller wing-like top section 92b and would be cut along the way by the cutting edges described above. The particular geometry of intake arm 90, which is bent downwardly 30 degrees from line A—A forward and bent 25 degrees in a forward fashion from line B—B on, has proved to be most advantageous in moving waste material from upper portion 104 of intake shredder unit 100 into lower chamber 102 and below, while at the same time cutting and preventing entanglement or compacting of material which, if it does occur, is easily freed up and loosened by reversal of the direction of rotation.

There is also shown in FIG. 8a and 8b a strip-off knife 198 which is attached to the underside of lower section 92a. Strip-off knife 198 has a triangular cross section with its tip pointing downward and the height of this triangular knife decreases from its lower portion to its top portion, i.e., nearer wing-like top section 92b. As material which might have become entangled is pulled radially upwardly, as dictated by the tapered shape of intake arm 90, strip-off knife 98 will assist in cutting such material as it is pulled across its triangular cutting tip.

While the shredder stack of the instant invention has been described herein only in the context of comminuting infectious hospital waste, it is apparent that it can also be used for a variety of other materials, for which much higher revolutions may be appropriate. While the preferred rotational speed for comminuting mixed and unsorted hospital waste is preferably in the 60 rpm range, the system may also be used for comminuting, e.g., only plastic refuse, in which case the rotational speed may be increased to upward of 800 rpm.

Thus, is apparent that there has been provided in accordance with the invention a method and apparatus, that fully satisfies the objects, aims, and advantages set forth above. While the invention has been described in conjunction with specific embodiments thereof, it is evident that many alternatives, modifications and variations will be apparent to those skilled in the art in light of the foregoing description. Accordingly, it is intended to embrace all such alternatives, modifications, and variations as fall within the spirit and broad scope of the appended claims.

I claim:

1. A process for sterilizing infectious waste comprising the steps of providing a sealable container containing rotatable comminuting means, a first closure means for said sealable container, connected to said sealable container a pumping means for removing gases, a sealable exit chamber, a second closure means for said sealable exit chamber and restrictable passage means for moving infectious waste material from said sealable container to said sealable exit chamber;

introducing infectious waste material into said sealable container containing rotatable comminuting means;

sealing said infectious waste material with said first closure means in said sealable container;

activating said second closure means for sealing said sealable exit chamber;

removing any gases contained in said sealable container by activating said pumping means until a predetermined vacuum level is achieved within said sealable container;

accumulating saturated steam from external steam generating means in a steam collection chamber outside said sealable container;

injecting said accumulated saturated steam into said sealable container and said sealable exit chamber until atmospheric pressure is restored therein;

injecting additional saturated steam into said sealable container and said sealable exit chamber until a predetermined pressure is reached therein; and activating said rotatable comminuting means for comminuting said infectious waste material within said sealable container and moving said infectious waste material through said restrictable passage means into said sealable exit chamber.

2. The process according to claim 1, wherein providing said sealable container has heatable walls that are maintained at a temperature above or at least equal to the temperature of the saturated steam employed.

3. The process according to claim 1, wherein said external pumping means is activated until a pressure of 100 mbar is reached within said sealable container.

4. The process according to claim 3, wherein said additional saturated steam is injected until a pressure of at least 15 psig and a temperature of at least 250° F. are reached within said sealable container.

5. The process according to claim 4, wherein said comminuting lasts for a period of 10 minutes.

6. The process according to claim 5, comprising the steps of repeating the sequence of steps of activating said pumping means, injecting said accumulated saturated steam, injecting said additional saturated steam and comminuting said infectious waste material a second time.

7. The process according to claim 6, comprising the steps of repeating said sequence of steps a third time.

8. The process according to claim 1, wherein said restrictable passage means is set to a predetermined size which the comminuted waste material must achieve before it is permitted to move from said sealable container to said second sealable exit chamber.

9. The process according to claim 8, wherein said sealable exit chamber has heatable walls that are maintained at a temperature above or at least equal to the temperature of the saturated steam employed.

10. The process according to claim 9, wherein said sealable exit chamber with a hydraulically gated exit port and hydraulic piston means for ejecting said comminuted waste material from said sealable exit chamber through said gated exit port;

said waste material is comminuted in said sealable container until it has all moved through said restrictable passage to said sealable exit chamber;

said pumping means is activated until the steam pressure within both said sealable container and said sealable exit chamber is reduced to atmospheric pressure; and said hydraulic piston means and said gated exit port are activated for removing said comminuted waste material from said sealable exit chamber.

11. The process according to claim 1, wherein said comminuting means includes a plurality of cutting means vertically above one another within said sealable container;

drive means located outside of said sealable container for said cutting means; and said drive means is activated in such a fashion that the direction of rotation is reversed intermittently during the comminuting step.

12. An apparatus for size reducing and sterilizing infectious waste, comprising a sealable treatment chamber for receiving infectious waste;

pumping means communicably connected to said sealable treatment chamber for removing gases from said sealable treatment chamber;

steam generating and storage means communicably connected with said sealable treatment chamber for pressurizing said sealable treatment chamber with saturated steam;

a plurality of rotatable comminuting means located along one common vertical axis within said sealable treatment chamber for size reducing said infectious waste by passing said infectious waste within said sealable treatment chamber in an axially downwardly fashion through said plurality of rotatable comminuting means while pressurizing said sealable treatment chamber with saturated steam; and a sealable chamber communicably connected to said sealable treatment chamber, said pumping means and said steam generating and storage means, into which said infectious waste is moved after it is passed through said plurality of rotatable comminuting means.

13. The apparatus according to claim 12, comprising heating means for said sealable treatment chamber for elevating and maintaining the inside wall temperature of said sealable treatment chamber above the boiling point of water.

14. The apparatus according to claim 12, comprising filter means communicably connected with said pumping means for removing particulate matters and deactivating noxious gases prior to venting said noxious gases to the ambient air.

15. The apparatus according to claim 12, further comprising passage means between said sealable treatment chamber and said sealable chamber for permitting said infectious waste to move from said sealable treatment chamber to said second sealable chamber when said plurality of rotatable comminuting means are activated.

16. The apparatus according to claim 15, further comprising valve means within said passage means between said sealable chamber and said second sealable treatment chamber for regulating the size to which said infectious waste must be reduced prior to passing from said sealable treatment chamber to said second sealable chamber.

17. The apparatus according to claim 15, further comprising a sealable exit gate within one of the walls of said second sealable chamber; and piston means within said sealable chamber for ejecting said infectious waste from said sealable chamber.

18. The apparatus according to claim 12, further comprising drive means located outside of said sealable treatment chamber for rotating said plurality of rotatable comminuting means; and shaft means for connecting said drive means with said plurality of rotatable comminuting means.

19. The apparatus according to claim 18, further comprising gear means between said drive means and said shaft means for regulating the speed and direction of rotation with which said drive means move said shaft means.

20. The apparatus according to claim 19, further comprising clutch means attached to said shaft means for engaging and disengaging said plurality of rotatable comminuting means from said drive means.

21. The apparatus according to claim 20, wherein said sealable treatment chamber further comprises
a pivotable lid;
sealably connected to a treatment section further comprising
an upper, conically shaped intake section which at its bottom is attached to
a cylindrical center section, which in turn is attached to
a second conus section; and
a bottom section having a floor plate and a top plate sealingly and detachably connected to said second conus section.

22. The apparatus according to claim 21, further comprising
sealing means within said floor plate of said bottom section for hermetically and thermally insulating said sealable treatment chamber from said drive means.

23. The apparatus according to claim 22, wherein said upper, conically shaped intake section of said treatment section further comprises
a plurality of stationary cutting means located along the inside wall of upper conically shaped intake section.

24. The apparatus according to claim 23, wherein said plurality of stationary cutting means further comprise
generally triangularly shaped knives, at least one which has its cutting surface pointing in the opposite radial direction from the others.

25. The apparatus according to claim 24, wherein said plurality of stationary cutting means are arranged in different vertical planes from one another.

26. The apparatus according to claim 25, wherein said cylindrical center section of said treatment section also comprises
one or more second stationary cutting means located along the inside wall of said cylindrical center section.

27. The apparatus according to claim 27, wherein said second stationary cutting means further comprise
generally triangularly shaped knives, at least one which has its cutting surface pointing in the opposite radial direction from the others.

28. The apparatus according to claim 27, wherein said second stationary cutting means are arranged in different vertical planes from one another.

29. The apparatus according to claim 28, wherein said plurality of rotatable comminuting means further comprise
at least one upwardly and generally radially outwardly extending intake rake means attached to said shaft means for moving said infectious waste in a pivotal downwardly fashion through said upper, conically shaped intake section of said sealable treatment chamber.

30. The apparatus according to claim 29, wherein said at least one upwardly and generally radially outwardly extending intake rake means further comprise
a base cylinder concentrically positioned upon such shaft means;
a radially upwardly pointing rake arm attached to said base cylinder;
cutting surfaces along the front edge and the rear edge of said radically upwardly pointing rake arm; and
said radically upwardly pointing rake arm upwardly and radially outwardly tapering down to a pointed winglet having cutting surfaces at its front, rear and circumferential side edges.

31. The apparatus according to claim 30, wherein said plurality of rotatable comminuting means further comprise
at least one rotary crusher means removably attached to said shaft means below said at least one upwardly and generally radially outwardly extending intake rake means; and
at least one stationary cutter disk located around said shaft means and biased against said at least one rotary crusher means for size reducing said infectious waste by cutting it through the rotational motion of said at least one rotary crusher means between the anterior and inferior surfaces of said at least one rotary crusher means and the upper surface of said stationary cutter disk.

32. The apparatus according to claim 31, wherein said at least one stationary cutter disk further comprises
an upper and horizontally planar outer annular surface;
a horizontal cutting edge at the same horizontal level as said outer annular surface which extends radially inwardly from said outer annular surface for a distance less than to the center of said at least one stationary cutter disk;
a radially inwardly and downwardly sloping spiral section extending from the radially interior edge of said horizontal cutting edge down to the lower annular bottom surface of said at least one stationary cutter disk, said radially inwardly and downwardly sloping spiral section generally defining an excentric circular axial opening through said at least one stationary cutter disk.

33. The apparatus according to claim 32, further comprising
at least one cylindrical cutter ring removably attached to said shaft means and located within said excentric circular axial opening of said stationary cutter disk, said at least one cylindrical cutter ring having a plurality of indentations within its outer cylindrical surfaces, the edges of which are sharpened to provide cutting surfaces.

34. The apparatus according to claim 33, further comprising
at least one spiral vane cutter removably attached to said shaft means below said at least one cylindrical cutter disk; and
a stationary cylindrical housing within which said at least one spiral vane cutter is rotated when said drive means are engaged.

35. The apparatus according to claim 34, further comprising
an exit port within the circumferential side wall of said stationary cylindrical housing for communicably connecting with said sealable chamber.

36. The apparatus according to claim 35, wherein said at least one spiral vane cutter further comprises
a plurality of horizontally planar spiral cutting edges defining between them radially outwardly and downwardly sloping surfaces for moving said infectious waste radially outwardly toward said exit port.

* * * * *